_United States Patent_ [19]

Kato et al.

[11] 3,999,505
[45] Dec. 28, 1976

[54] APPARATUS FOR AUTOMATIC APPLICATION OF BLOOD SERUM

[75] Inventors: Yutaka Kato, Tama; Teruo Ouchi; Hirohiko Tokitoh, both of Hachioji, all of Japan

[73] Assignee: Olympus Optical Co., Ltd., Tokyo, Japan

[22] Filed: June 3, 1975

[21] Appl. No.: 583,266

[30] Foreign Application Priority Data
June 8, 1974 Japan .............................. 49-64585
Sept. 27, 1974 Japan ............................ 49-110604

[52] U.S. Cl. .................................. 118/7; 118/203;
118/224; 118/249; 118/243
[51] Int. Cl.² ...................... B05C 1/16; B05C 1/08
[58] Field of Search .............. 118/242, 7, 243, 263,
118/73, DIG. 23, 203, 104, 224, 249, 401;
354/318; 23/253 R, 230 B, 258.5

[56] References Cited
UNITED STATES PATENTS

| | | | |
|---|---|---|---|
| 2,333,369 | 11/1943 | Glickman | 118/203 |
| 3,332,394 | 7/1967 | Cooke | 118/263 |
| 3,351,040 | 11/1967 | McCall | 118/249 |
| 3,589,938 | 6/1971 | Blewett et al. | 118/401 X |
| 3,616,472 | 11/1971 | Boyle et al. | 118/224 |
| 3,888,206 | 6/1975 | Faulkner | 118/100 |

_Primary Examiner_—John P. McIntosh

[57] ABSTRACT

An apparatus for automatic application of blood serum comprises an applicator, a rinsing unit and a drip both associated with the applicator, means for conveying a blood serum bearing film while maintaining it in opposing relationship with the applicator, and means for supplying a buffer solution for wetting the film with a buffer solution prior to the application of a blood serum thereto. Blood serum is automaticaly applied to the film which is previously wetted with the buffer solution in an automatic manner.

6 Claims, 11 Drawing Figures

APPARATUS FOR AUTOMATIC APPLICATION OF BLOOD SERUM

BACKGROUND OF THE INVENTION

The invention relates to an apparatus for automatic application of blood serum, and more particularly to such apparatus for use in a blood serum analyzer of cataphoretic type in which a blood serum applied to a serum bearing film, which is used for producing a specimen, is fractionated into components by a cataphoresis process and then the fractions are subjected to a determination with a densitometer or filter photoelectric colorimeter for the purpose of quantitative analysis of the serum components.

In a cataphoretic serum analyzer, it is necessary that a buffer solution be coated on the serum bearing film before the serum is applied to the film in order to render the film in a condition readily susceptible to the cataphoretic process. Usually, a cellulose acetate film is often used as the serum bearing film. However, the cellulose acetate film has a multitude of fine pores, so that if it is directly immersed into a buffer solution, the bubbles in the pores will be confined therein by the solution, to remain as white spots. When the serum is subsequently applied to the film and electrically energized to effect a cataphoretic process, the presence of the remaining air prevents a cataphoretic movement of the serum components and thus precludes a smooth formation of fractionated patterns. To avoid such difficulty, it has been the practice to immerse the film in the buffer solution by floating a support on the surface of the solution and to submerge it gently thereinto, so as to avoid trapping of the air bubbles. Subsequent to the immersion, the film is removed from the solution and is held sandwiched between a pair of paper filters to absorb an excess amount of the solution before the film is passed to the serum application and the energization steps. Thus, the immersion and the removal of excessive liquid require a considerable length of time and a certain degree of skill with attendant care, which stood in the way of automation of the process steps.

In the automation of the serum application, it will be most favorable that the same applicator be used repeatedly. This requires that the applicator be rinsed and dripped after each serum application. Because of the troublesome operation which must be performed on the serum applicator, efforts towards automation of the application have been unsuccessful, and instead a blood serum has been introduced into a micro pipette to draw a line therewith for the purpose of applying the serum. However, such an application operation requires a high level of skill, and must be carefully performed by a skilled operator. Moreover, an accurate determination is prohibited unless the serum application is achieved in a proper manner.

SUMMARY OF THE INVENTION

It is a first object of the invention to provide an apparatus for automatic application of blood serum including a buffer solution supply device which essentially comprises a pair of rollers, at least one of which has its surface formed of a sponge material.

In accordance with the invention, a time and labor consuming operation which has been adopted in the prior art is replaced by a fully automated process of feeding a serum bearing film through the nip of a pair of rollers which supply a sufficient amount of the buffer solution to the film and which also remove an excess amount of the liquid therefrom. While the prior art practice involved a waste of the buffer solution because an amount thereof absorbed by the paper filters has been disposed of, in accordance with the invention, the excess amount of the buffer solution which is removed from the film is returned to the rollers by absorption, thereby avoiding such waste. The apparatus is compact and simple in arrangement, and reduces the time required for the application of the blood serum.

If a vessel containing the buffer solution is made separate from the rollers, it can be covered with a suitable lid to minimize the evaporation of the buffer solution therefrom and to permit a continued application over a prolonged period of time. The separate provision of the vessel avoids the requirement for an additional space.

It is a second object of the invention to provide an apparatus for automatic application of blood serum which, in addition to the buffer solution supply device, includes a drip device which moves a paper filter in timed relationship to the operation of the serum applicator so that a fresh portion of the paper filter is maintained in opposing relationship with the applicator.

The drip device used in the apparatus of the invention permits rinsing water adhering to the serum applicator to be completely removed by the paper filter. Portions of the paper filter which have been once used are moved out of the drip device by the time the applicator returns to it upon completion of the serum application and rinsing steps, so that the drip device can be repeatedly used while assuring a satisfactory dripping operation. The drip device contributes to the automation of the apparatus according to the invention. While it may appear that the air may be blown against the portion of the applicator to which the rinsing water remains, it is impossible to completely remove the rinsing water within a short period of time. After conducting various experiments, it is found that the dripping can be achieved most reliably and within the shortest period of time by absorption of the rinsing water remaining on the applicator by urging the latter against the paper filter.

DETAILED DESCRIPTION OF PREFERRED EMBODIMENTS

Figure 1:
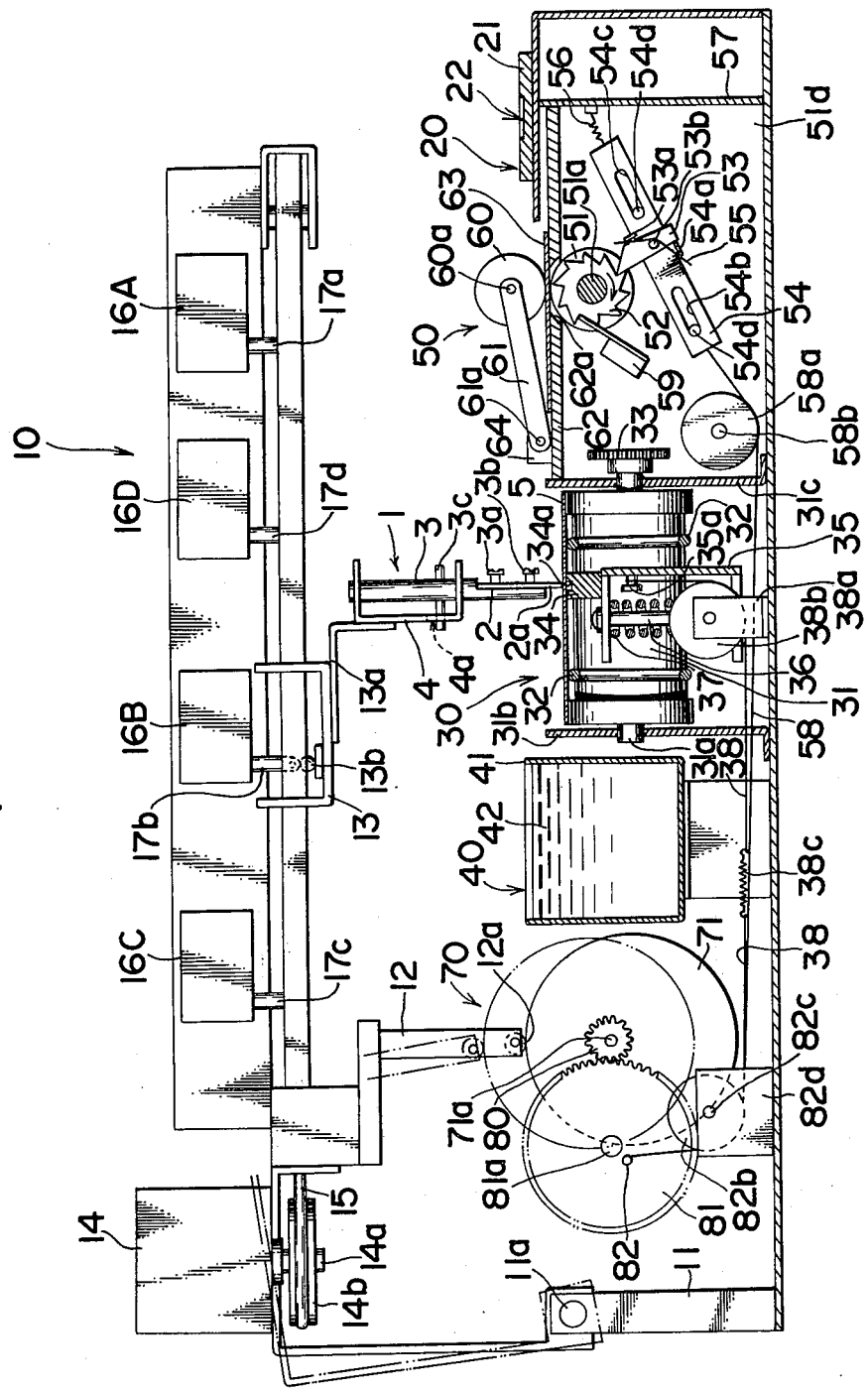
FIG. 1 is an elevational cross section of the apparatus for automatic application of the blood serum constructed in accordance with one embodiment of the invention.

Referring to FIG. 1, there is shown the apparatus for automatic application of the blood serum constructed according to the invention. Generally, the apparatus comprises a guide 10 along which a serum applicator 1 is moved to the right or left as viewed in this Figure; a serum supply station 20 where the serum is supplied to the applicator; a serum application station 30 where the serum is applied from the applicator to a serum bearing film 5, a rinsing station 40 where the applicator is rinsed, a drip station 50 where the drip device according to the invention is incorporated, and a cam assembly 70 which moves the guide 10 in the vertical direction.

Figure 2:
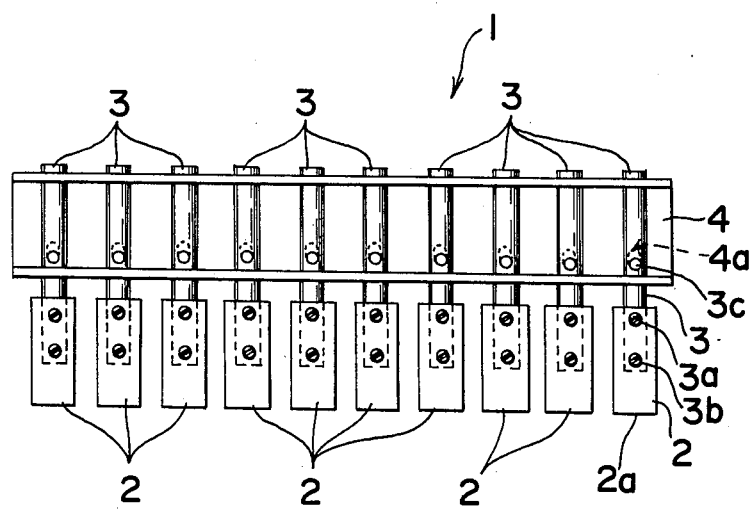
FIG. 2 is a front view of an example of the serum applicator.

Construction of the applicator 1 is fully shown in FIG. 2 wherein it will be noted that the applicator 1 comprises a plurality of penpoint-like members 2 having a narrow groove in its forward end 2a and secured to stems 3 by set screws 3a, 3b, the stems being mounted on a support arm 4. A serum is applied to the forward end 2a of the respective member 2, which is then lightly urged against the film 5 for application thereto. Pins 3c fixedly mounted on the stems 3 engage vertically elongated slots 4a formed in the support arm 4 for vertical movement thereof.

Returning to FIG. 1, a post 11 is shown at the left-hand side of the Figure for pivotally mounting the guide 10 on a pivot 11a. An arm 12 carrying a roller 12a at its free end is secured to the guide 10 by suitable means, and a carriage 13 having the applicator 1 secured thereto by means of a mounting plate 3a is disposed for movement in the lateral direction along the guide 10, and is adapted to be driven by a rope 15 which extends around a pulley 14b that is in turn fixedly mounted on the shaft 14a of a motor 14. A plurality of microswitches 16A, 16B, 16C and 16D having unidirectionally operating actuators 17a, 17b, 17c and 17d, respectively, are disposed at selected positions corresponding to the serum supply station 20, the serum application station 30 and the like, and are operated when the carriage 13 moves to the respective switch position. By way of example, the microswitch 16B is shown operated when a pusher 13b secured to the carriage 13 presses against the associated actuator 17b. These microswitches control the rotation of the motor 14 and hence the movement of the carriage 13.

A dish 21 is disposed in the serum supply station 20, and includes a number of recesses 22 which are equal in number to the number of the applicator members 2 and which receive the serum to be examined.

The serum application station 30 includes a pair of rollers 31 which have their shafts 31a rotatably mounted in a pair of support plates 31b and 31c. The rollers divide the length through which the applicator 1 extends into substantially equal intervals. A plurality of conveying belts 32 extend around the rollers, and a gear 33 is coupled to the same shaft as the rollers 31 and is rotated by suitable means, not shown, for operating the rollers 31 and belt 32 to convey the serum bearing film 5 in a direction perpendicular to the plane of the sheet. A retainer in the form of an elongate bar having the length corresponding to that of the applicator 1 is formed with a longitudinally extending groove 34a in its top surface, and is secured to and supported by holder 35 which is vertically slidably mounted on a shaft 36 and which is normally urged upward by a spring 37 disposed around the shaft. A wire 38 has its one end secured to a bolt 35a which is fixedly mounted on the holder 35 at a suitable location, and extends around a pulley 38b which is rotatably mounted on a mount 38a. As will be described later, by pulling the wire 38 to the left, the holder 35 can be lowered against the resilience of the spring 37, thus also lowering the retainer 34.

The rinsing station 40 where the applicator members are rinsed includes a vessel 41 containing a supply of rinsing water 42.

Figure 3:
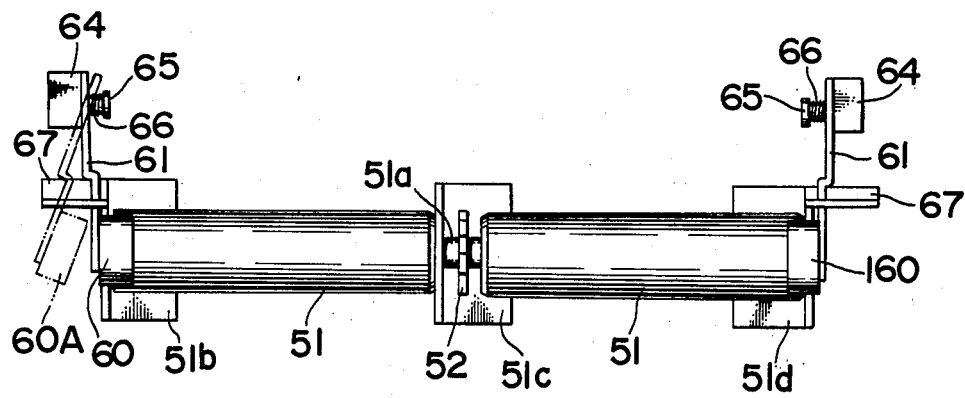
FIG. 3 is a plan view showing the relationship between the paper filter feed roller and the retaining rollers.
Figure 4:
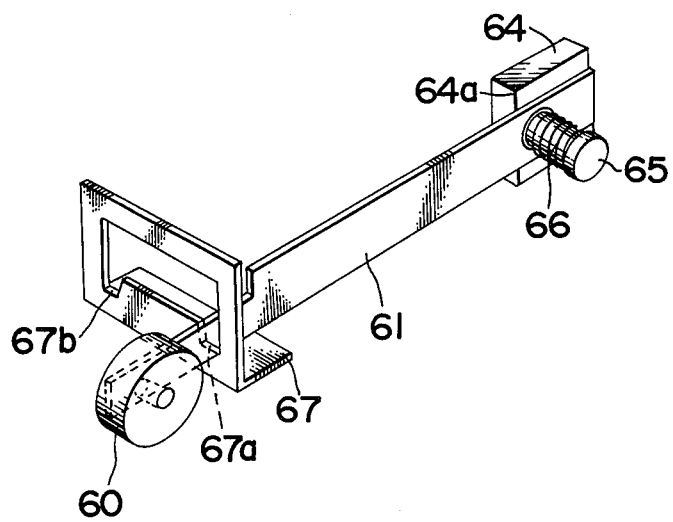
FIG. 4 is a perspective view of support means for the retaining roller.

The drip station 50 includes a paper filter feed roller 51 which comprises a pair of elongate sections as will be noted from FIG. 3 which shows a plan view thereof. The roller 51 has its shaft 51a supported by support plates 51b, 51c and 51d, and intermediate its two sections, a ratchet wheel 52 is mounted on the shaft 51a. A pawl 53 is pivotally mounted on a support piece 54 at pivot 53a, and is urged for clockwise rotation by a spring 55 which has its opposite ends engaged with a projection 53a on the pawl 53 and a projection 54a on the support piece 54, respectively. However, the rotation of the pawl 53 is prevented by the engagement of its end against the projection 54a. The support piece 54 is formed therein with a pair of elongated slots 54b and 54c which are engaged by a pair of stationary pins 54d. A spring 56 has its one end secured to one end of the support piece 54 while its other end is anchored to a partition 57. A wire 58 has its one end secured to the other end of the support piece 54, and extends around a pulley 58a which is rotatably mounted on a stationary shaft 58b. It will be appreciated that the wire can be operated to cause movement of the support piece 54 over an extent as permitted by the engagement between the slots 54b, 54c and the pins 54d, thus causing a movement of the pawl 53. As will be further described later, the wire 58 can be pulled to the left to disengage the pawl 53 from the ratchet wheel 52 so as to permit an incremental rotation of the latter corresponding to one tooth pitch thereof. This results in a corresponding incremental rotation of the roller 51. The ratchet wheel is also engaged by a detent piece 59 which prevents a reverse rotation thereof. A pair of rollers 60, 160 (see FIG. 3 for the roller 160) are disposed above the opposite ends of the roller 51, which extends slightly above the surface of a base 62 through a notch 62a formed therein so as to be in abutting relationship with the rollers 60, 160. The rollers 60, 160 have their axles 60a rotatably mounted on a pair of support rods 61. When a paper filter 63 is disposed on the surface of the base 62 as shown in FIG. 1, it is held sandwiched between the roller 51 and the pair of rollers 60, 160. As indicated in FIG. 1, one of the support rods, 61, which carries the roller 60 is made so as to be pivotal about an axle 61a so that the roller 60 can be moved vertically, thereby facilitating the placement of the paper filter 63 on the surface of the base 62. However, in the preferred embodiment, in order to further facilitate the placement of the paper filter 63, the other end of the support rod 60 which rotatably carries the retaining roller 60 is mounted on a rectangular mount 64 by a pin 65 in a manner such that it can be moved pivotally about the mount and lengthwise of the pin 65, and is normally urged by a spring 66 against the mount, as shown in FIGS. 3 and 4. A guide frame 67 is disposed adjacent to the retaining roller 60, and as indicated in FIG. 4, the support rod 61 can be manually moved therein from a recess 67a to another recess 67b, both formed in the frame. Such movement of the support rod 61 results in a movement of the retaining roller 60 to a position 60A shown in phantom lines (see FIG. 3), the rod 61 angularly moving about one edge 64a of the mount 64 and the other end thereof moving to the right against the resilience of the spring 66, thereby positioning its opposite end in the recess 67b. When the rod 61 is positioned within the recess 67b of the frame 67, it can be returned to the recess 67a under the resilience of the spring 66 by raising it manually. The same arrangement is employed in conjunction with the other roller 160, but will not be repeated.

Figure 5:
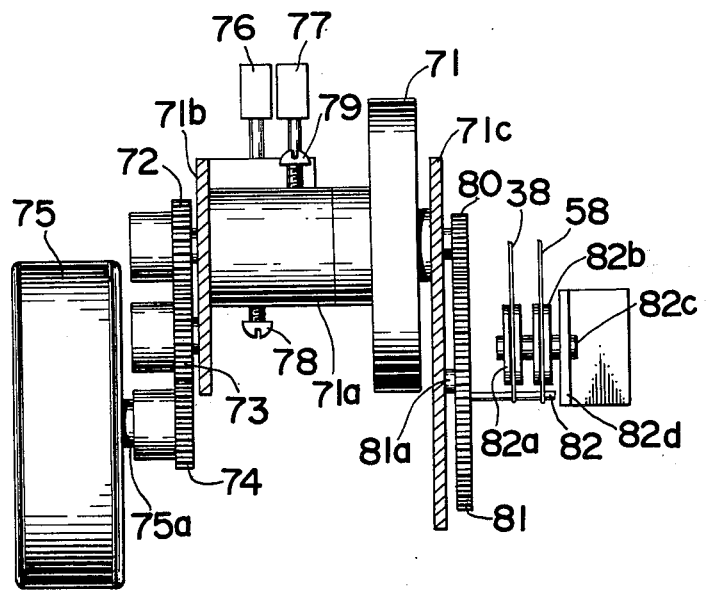
FIG. 5 is a plan view of a cam assembly.

FIG. 5 shows a specific construction of the cam assembly 70 in plan view. The assembly includes an eccentric cam 71 having a rotary shaft 71a which is supported by a pair of support plates 71b, 71c and on which is fixedly mounted a gear 72, which is in turn operatively connected with the rotary shaft 75a of a motor 75 through a pair of transmission gears 73 and 74. A pair of microswitches 76 and 77 are disposed so as to be operated by a pair of pins 78 and 79 which are fixedly mounted on the rotary shaft 71a of the eccentric cam 71. The microswitch 76 serves to interrupt the operation of the motor 75 and initiating the operation of the motor 14 while the microswitch 77 operates during a particular phase of movement of the serum applicator 1 as will be described later to interrupt the operation of the motor 75 for a while, which is again set in motion at a given period of time determined by a timer. During such period of time, both motors 14 and 17 remain at rest. The assembly also includes a gear 80 fixedly mounted on the shaft 71a of the cam 71 and which meshes with a reduction gear 81 mounted on a shaft 81a, the gear ratio of these gears being 1:4. The gear 81 has a pin 82 fixedly mounted thereon at a position spaced from the axis thereof, and the wires 38 and 58 which serve operate the retainer 34 and the feed roller 51 are connected with the pin 82 through the interposition of a pair of coaxial pulleys 82a, 82b of an equal diameter and mounted on a common shaft 82c which is in turn supported by a support plate 82d. It will be understood that the rotation of the eccentric cam 71 results in a revolution of the pin 82 about the axis 81a, thereby loosening or tensioning the wires 38, 58 for vertically moving the retainer 34 or feeding the paper filter 63. It will be noted from FIG. 1 that a buffering spring 38c is connected intermediate the length of the wire 38.

The operation of the apparatus described begins with locating the applicator 1 over the dish 21. When the motor 75 is set in motion, the rotation of the eccentric cam 71 results in a substantially upward vertical motion of the arm 12, which in turn causes the guide 10 to be rocked vertically about the mounting shaft 11a between the positions shown in phantom lines and in solid line, respectively. In the solid line position where the applicator 1 assumes its lowermost position, the forward end of the applicator members 2 will be inserted into an amount of serum to be examined which is received in the recesses 22 formed in the dish 21, thus supplying the serum to the end 2a of the member 2. Upon completion of one revolution of the eccentric cam 71 to return to the position shown in phantom lines, the microswitch 76 operates to interrupt the motion of the motor 75, while the motor 14 is set in motion. Thereupon, the carriage 13 moves to the left together with the applicator 1. When the carriage 13 moves to the position of the microswitch 16B, the carriage 13 urges against the contact 17b to operate the microswitch 16B, whereby the motor 14 and hence the carriage 13 come to a rest. Simultaneously, the motor 75 is set in motion initiating the vertical movement of the arm 12 concurrently with loosening the wire 38, whereby the retainer 34 is raised together with the holder 35, allowing the application of the serum as indicated in FIG. 1. The vertical movement of the applicator 1 activates the microswitch 76 in the same manner as mentioned before to interrupt the rotation of the motor 75, while the motor 14 is set in motion to move the carriage 13 to the next step where it is stopped by the operation of the actuator 17c for microswitch 16C. While the microswitch 16C is not shown with a contact which corresponds to the contact 17b associated with the microswitch 16C, it should be understood that the construction operation of the microswitch 16C is quite similar to the microswitch 16B. In this manner, the various steps are performed in a sequential manner before reaching the dripping step.

When the rinsing step is completed and the carriage is in its up position, the microswitch 76 operates to move the carriage 13 in the reverse direction, which movement is interrupted by the operation of the microswitch 16D and the applicator 1 is caused to descend. Thereupon, the forward end 2a of the member 2 of the applicator 1 is brought into contact with a paper filter 63 which is disposed in the drip station 50. The paper filter 63 absorbs the rinsing water which adheres to the penpoint-like member as a result of the rinsing step. To avoid the difficulty that the rinsing water can not be completely absorbed during an instantaneous period of contact between the member 2 and the paper filter 63 during the vertical movement of the applicator 1, the microswitch 77 operates to interrupt the rotation of the motor 75 when the member 2 comes into contact with the paper filter 63, and a timer is used to restart the motor 75 after a given period of time, thereby assuring a complete absorption of the rinsing water by the paper filter 63. The paper filter 63 which has absorbed the rinsing water can not be used during the next dripping operation. However, in the apparatus of the invention, the eccentric cam 71 undergoes four revolutions during the time interval from the supply of the serum to the dripping of the applicator. As a result, the reduction gear 81 undergoes one revolution during such period, so that the wire 58 cooperates with the pawl to permit a rotation of the roller 51 corresponding to one tooth pitch of the ratchet wheel 52. The rotation of the roller 51 results in a movement of the paper filter 63 through a given distance to the right as viewed in FIG. 1, so that a fresh, non-wetted portion of the paper filter 63 is located with respect to the forward end 2a of the member 2 when the applicator 1 descends the next time.

The serum bearing film 5 which has been fed into the serum application station 30 and supplied with the serum is transferred to the cataphoresis step by the time the rinsing and dripping steps of the applicator is completed. Then a fresh film is conveyed into the application station by the belts 32. It will be appreciated that for each cycle of operation, the roller 51 is rotated through an increment corresponding to one pitch of the ratchet wheel 52 to feed the paper filter 63 by a given distance to present a fresh, non-wetted portion thereof for the next dripping operation. When the entire paper filter is exhausted, it can be replaced by a fresh one.

The replacement is facilitated by moving the support rod 61 into the recess 67b (see FIG. 4) formed in the guide frame 67, thereby enabling removal of the used paper filter. When a fresh paper filter is placed over the base 62, it is only necessary to disengage the support rod 61 from the recess 67b, whereupon the spring 66 returns it to the original recess 67a, again retaining the marginal edge of the paper filter now placed.

Figure 6:
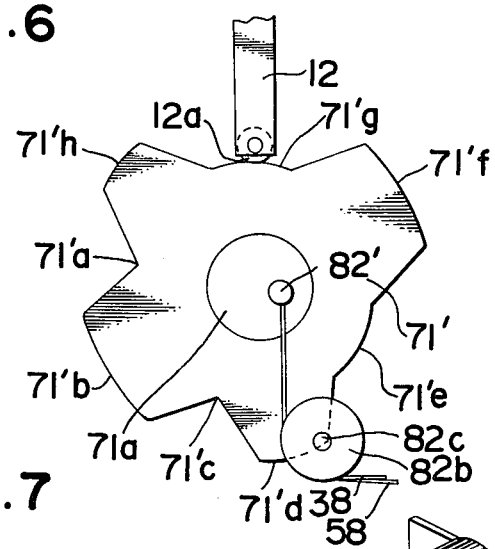
FIG. 6 is a front view of another example of the cam assembly.

FIG. 6 shows another example of the cam assembly 70 which includes a profiled cam 71' in place of the eccentric cam 71. The cam 71' includes a plurality of recesses 71'a, 71'c, 71'e and 71'g which lie on a common circumference of a reduced diameter than that of another circumference on which a plurality of cam lobes 71'b, 71'd, 71'f and 71'h lie. When the arm 12 bears against one of the cam recesses, the guide 10 is in its lower position, while the guide 10 is in its upper position when the arm 12 bears against one of the cam lobes. With this cam assembly, no reduction gear is used, and instead the wires 38 and 58 are directly connected with a pin 82' on the cam 71'. In other respects, the described cam assembly is similar to the previous one.

The operation of the apparatus incorporating the cam assembly which includes the cam 71' will be described briefly. The operation starts with the abutting engagement of the arm 12 against the cam lobe 71'h, which corresponds to the position of the carriage 13 in which it activates the microswitch 16A or to the location of the applicator 1 in the serum supply station 20. As the motor 75 rotates to rotate the cam 71', the arm 12 bears against the cam recess 71'a, whereby the arm 12 descends together with the guide 10 and the applicator 1 for providing a supply of the serum to the applicator. As the cam 71' further rotates to cause the arm 12 to bear against the cam lobe 71'b, the applicator 1 is raised. By suitably locating pins 78 for operating the microswitch 76 in the various steps so as to control the rotation of the motor 14, the carriage 13 is moved along the guide together with the applicator 1. The operation of the microswitches, such as that of the microswitch 16B to stop the carriage 13, is completely similar to the operation previously described. In this manner, all of the steps beginning with the supply of the serum until the dripping can be repeatedly performed in a sequential manner. It will be noted that the length of the cam recesses 71'a, 71'c, 71'e and 71'g can be determined so as to provide the necessary operation time in the various steps while the length of the cam lobes 71'b, 71'e, 71'f and 71'h can be adjusted to the required time of movement of the applicator 1 between adjacent steps.

When one cycle of operation is completed by one revolution of the cam 71', the wire 58 is pulled through a given distance to feed the paper filter 63 by a given distance to thereby present a fresh portion thereof at the dripping position for the applicator 1 in the same manner as mentioned previously. It is to be noted that the serum bearing film 5 is subjected to a pretreatment by a buffer solution applicator device to be described below prior to the application of the serum thereto by the serum applicator 1.

Figure 7:
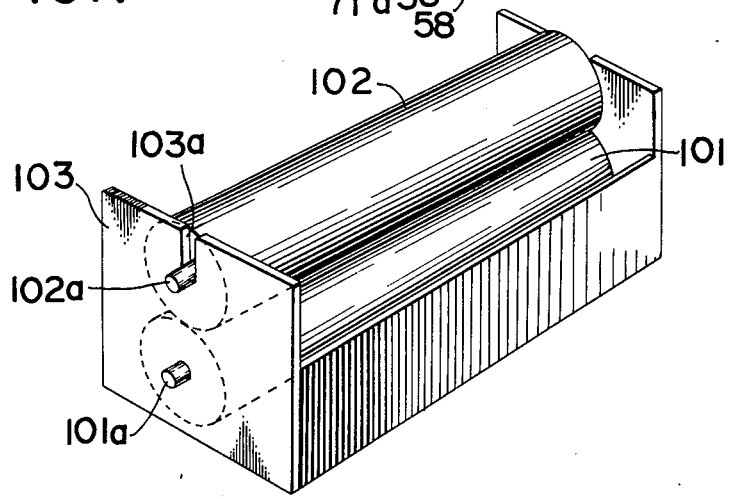
FIG. 7 is a perspective view of the buffer solution supply device.
Figure 8:
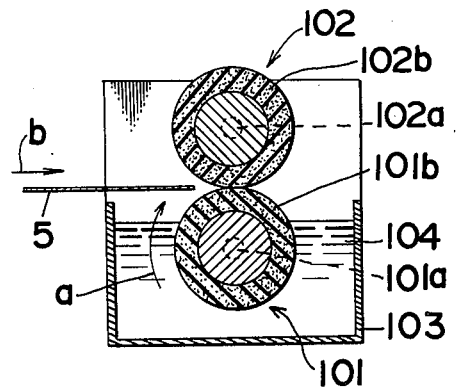
FIG. 8 is a transverse cross section of the device shown in FIG. 7.

Referring to FIG. 7, the buffering solution applicator device comprises a pair of rollers 101 and 102 having their shafts 101a and 102a rotatably mounted in the opposite sidewalls of a casing 103, the shaft 102a being received in a notch 103a formed in the casing. At least the surface portions 101b and 102b of these rollers are formed of a sponge material. As will be seen in FIG. 8, the casing 103 contains a supply of buffer solution 104 which may comprise Veronal-Veronal soda, and the roller 101 is partly immersed into the buffering solution 104. The shaft 101a of the roller 101 is adapted to be rotated by suitable means, not shown. When the film 5 which comprises a cellulose acetate sheet is inserted into the nip between the rollers 101 and 102, the rotation of the roller 101 in the direction indicated by arrow a causes the film 5 to be fed in the direction of arrow b or from left to right, as viewed in this Figure.

Figure 9:
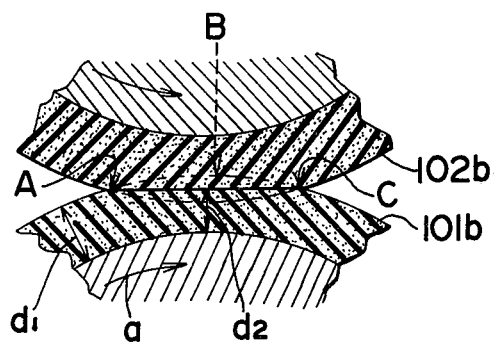
FIG. 9 is a fragmentary enlarged cross section illustrating the manner of operation of the buffer solution supply rollers.

In operation, the serum bearing film 5 to be wetted with the buffer solution is inserted into the nip between the both rollers 101, 102, and the roller 101 rotated in the direction of the arrow a (see FIG. 9), whereby the film 5 is moved from left to right. Since the roller 101 is partly immersed into the buffer solution 104 and its surface portion 101b is formed of a sponge material, the latter contains an amount of the buffering solution. Thus, as the film 5 is fed by the rollers 101, 102, it is wetted by the buffering solution contained within the roller 101. FIG. 9 shows the region of contact between the rollers 101, 102 to a greater scale, and it will be noted in this Figure that the effect of gravity upon roller 102 compresses the surface sponge portions 101b and 102b of both rollers from their normal thickness $d1$ to a smaller thickness $d2$, whereby the buffering solution contained within the surface portion 101b of the roller 101 is squeezed therefrom for satisfactory wetting of the film 5 therewith. More specifically, the buffering solution contained within the roller 101 will be squeezed therefrom to wet the film 5 during movement of the film 5 from a point A where the contact between the rollers is initiated to a point B which lies in the center of the region of contact, while an excess amount of the solution will be removed from the film by the both rollers during its movement from the point B to a point C where the contact therebetween ends. While in the embodiment shown, both rollers are provided with a surface sponge portion, it will be appreciated that only the roller 101 immersed into the buffering solution 104 or the other roller 102 may be provided with such a sponge portion. However, the provision of the sponge portions on both rollers as in the embodiment shown is more effective to the removal of the excess amount of the buffering solution from the film. The sponge portions can be compressed by other means than by the effect gravity upon roller 102.

Figure 10:
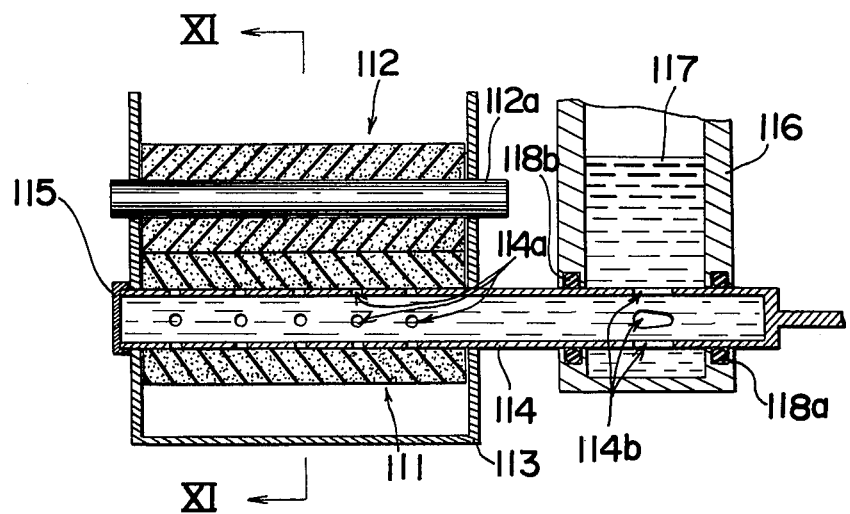
FIG. 10 is a cross section of another example of the buffer solution supply device.
Figure 11:
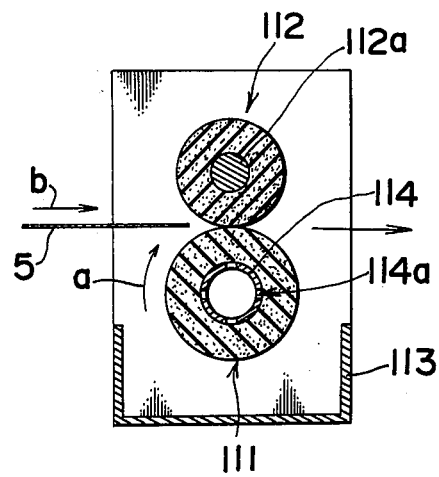
FIG. 11 is a cross section taken along the line XI—XI shown in FIG. 10.

FIGS. 10 and 11 show another example of the buffering solution applicator device which can be used in the invention. The device includes a pair of rollers 111 and 112, both formed of a sponge material and disposed in abutting relationship against each other. A buffering solution is supplied to the roller 111 by penetration from inside the roller. Specifically, the roller 111 has a hollow shaft 114 which is formed with a number of perforations 114a and which is closed at its one end by a plug 115. A vessel 116 containing a supply of buffering solution 117 is disposed close to the roller 111, and the hollow shaft 114 extends through the vessel. A pair of O-rings 118a, 118b are disposed in the interface between the shaft 114 and the walls of the vessel 116. In the region within the vessel 116, the shaft 114 is formed with openings 114b which permit the buffering solution 117 contained in the vessel to be admitted into the hollow space of the shaft 114. It will be noted that a casing 113 for the rollers constitutes a drainage container. In operation, the rotation of the shaft 114 by a suitable motor, not shown, permits the buffering solution 117, which finds its way into the hollow space of the shaft 114 through the openings 114b, to penetrate into the roller 111 for supplying it to the film 5. It will be noted that the rollers also function to remove an excess amount of buffering solution from the film, and to drain it through the casing 113. It will be understood that the rollers 111, 112 are operated by suitable means, operating in conjunction with the cam assembly 70, in timed relationship with the other stations 20, 30, 40 and 50.

What is claimed is:

1. An apparatus for automatic application of blood serum comprising guide means, a serum applicator movable along the guide means; drive means for moving the applicator to a serum supply station, a serum application station and a rinsing station in sequence, said stations being arranged at closely spaced intervals and adjacent to the guide means, and a dripping device associated with the applicator and positioned adjacent to at least one of the stations, the dripping device including a paper filter for removing by absorption of rinsing water adhering to the applicator, and at least one roller disposed for contact with at least one surface of the paper filter for causing a movement thereof, said dripping device being effective to contact the applicator which has been subjected to an operation in the rinsing station by bringing a forward end of the applicator into abutment against the paper filter, said paper filter being moved by a given distance by rotating the roller for a limited time interval during the movement of the applicator through the various stations, thereby presenting a fresh portion of the paper filter for abutment by the applicator.

2. Automated apparatus for applying a measured sample of serum to a substrate for subsequent testing comprising:
   means for applying a buffering solution to said substrate;
   applicator means;
   a serum supply station;
   an application station; said supply and application stations being arranged at closely spaced intervals;
   means for moving the buffered substrate from said buffer applying means to said application station;
   guide means positioned above said stations and adapted to guide the applicator means past all of the stations;
   means for sequentially moving said applicator means along said guide means, which define a first linear path, to said serum supply station and said application station;
   means responsive to positioning of the applicator means above each station for halting the applicator means; and means responsive to halting of the applicator means for reciprocally moving said applicator means in a direction transverse to said first linear path to sequentially enable the applicator means to pick up a measured amount of serum at the supply station and deposit said serum upon said substrate at the application station.

3. The apparatus of claim 4 wherein said buffering solution applying means includes a pair of rollers disposed in abutting relationship with each other, at least one of the rollers having its surface portion formed of a sponge material, the device also including a hollow shaft which carries said one roller and formed with a plurality of apertures for permitting penetration of a buffering solution into said one roller through the hollow shaft, said rollers operating to feed a serum bearing film through the nip therebetween and to wet it with the buffering solution which has penetrated through said one roller, the surface portion of said one roller being effective to remove by absorption an excess amount of buffering solution from the film as the rollers are disengaged from their abutting relationship.

4. The apparatus of claim 2, further comprising a rinsing station containing a rinsing solution and arranged at a closely spaced interval relative to one of said supply and application stations;
   said application moving means further comprising means for sequentially moving said applicator means along said first linear path from said application station to said rinsing station;
   said halting means being further adapted to halt the applicator means when positioned above the rinsing station; and
   said reciprocating means further being adapted to move said applicator means into and out of said rinsing solution when the applicator means is halted at the rinsing station.

5. The apparatus of claim 4, further comprising a drip station; said drip station comprising means for incrementally moving an elongated absorbing substrate along a second linear path;
   said applicator moving means further comprising means for moving said applicator means along said first linear path from said rinsing station to said drip station;
   means responsive to movement of the applicator means adjacent the drip station to halt said applicator means;
   said reciprocating means including means responsive to halting of the applicator means and adapted to move said applicator means into and out of engagement with said absorbing substrate to dry said applicator means preparatory to the next serum application and rinsing operations whereby said incremental moving means advances an unused portion of said absorbing substrate into position for the next drying operation.

6. The apparatus of claim 2, wherein said buffering solution applying means comprises a pair of rollers disposed in abutting relationship with each other, at least one of the rollers having its surface portion formed of a sponge material, said one roller being maintained immersed in a supply of buffering solution, said pair of rollers operating to feed a serum bearing surface through the nip therebetween while wetting it with the buffering solution, the surface portion of said one roller being effective to remove by absorption an excess amount of buffering solution from the film as the rollers are disengaged from their abutting relationship.

* * * * *